(12) United States Patent
Burgess et al.

(10) Patent No.: US 12,082,951 B2
(45) Date of Patent: *Sep. 10, 2024

(54) SHARPS CONTAINER

(71) Applicant: Medline Industries, LP, Northfield, IL (US)

(72) Inventors: James Burgess, Lake Bluff, IL (US); Scott Bedoe, McHenry, IL (US); Hongmeng Tian, Shenzhen (CN)

(73) Assignee: Medine Industries, LP, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,163

(22) Filed: Jan. 19, 2023

(65) Prior Publication Data

US 2023/0149110 A1    May 18, 2023

Related U.S. Application Data

(63) Continuation of application No. 16/845,842, filed on Apr. 10, 2020, now Pat. No. 11,559,369, which is a continuation of application No. 16/436,920, filed on Jun. 11, 2019, now Pat. No. 10,617,485, which is a
(Continued)

(51) Int. Cl.
| | | |
|---|---|---|
| *A61B 50/36* | (2016.01) | |
| *A61B 50/00* | (2016.01) | |
| *A61B 50/37* | (2016.01) | |

(52) U.S. Cl.
CPC ............ *A61B 50/36* (2016.02); *A61B 50/362* (2016.02); *A61B 50/37* (2016.02); *A61B 2050/005* (2016.02); *A61B 2050/375* (2016.02)

(58) Field of Classification Search
CPC ....... A61B 50/37; A61B 50/36; A61B 50/362; A61B 2050/0083; A61B 50/00; B65F 1/10
See application file for complete search history.

(56) References Cited

U.S. PATENT DOCUMENTS

| | | |
|---|---|---|
| 2,351,597 A | 6/1944 | Burlin |
| 2,634,933 A | 4/1953 | Grimsley |
| 2,667,320 A | 1/1954 | Whitley |
| (Continued) | | |

FOREIGN PATENT DOCUMENTS

| | | |
|---|---|---|
| AU | 686587 B2 | 2/1998 |
| DE | 890623 C2 | 9/1953 |
| (Continued) | | |

*Primary Examiner* — Jeffrey R Allen
(74) *Attorney, Agent, or Firm* — Gurr Brande & Spendlove, PLLC; Robert D. Spendlove

(57) ABSTRACT

A container for disposal of medical waste is provided that comprises a receptacle with an open top. A lid is attached to the receptacle to cover the open top of the receptacle. The lid has an elongated opening sized to permit the introduction of medical waste into the receptacle. A closure flap is connected to the lid to selectively close the lid opening. The closure flap is movable between an open position, a closed position, and a locked position. The closure flap is attached to the lid by axial hubs that extend from each side of the closure flap through openings in the side walls of the lid. Covers attached to the outside of the side wall of the lid and engaged with the closure flap axial hub. The container may also include a locking external cabinet that encloses the receptacle and can be mounted to a wall.

18 Claims, 11 Drawing Sheets

Related U.S. Application Data continuation of application No. 14/921,586, filed on Oct. 23, 2015, now Pat. No. 10,321,968.

(56) References Cited

U.S. PATENT DOCUMENTS

| | | |
|---|---|---|
| 3,041,030 A | 6/1962 | Heimrich |
| 3,064,931 A | 11/1962 | Rowe |
| 3,208,706 A | 9/1965 | Clark |
| 3,333,721 A | 8/1967 | Marek |
| 3,347,507 A | 10/1967 | Dyer |
| 3,817,448 A | 6/1974 | Schneider |
| 3,869,979 A | 3/1975 | Sulcek |
| 3,981,436 A | 9/1976 | Neal |
| 4,338,987 A | 7/1982 | Miles |
| 4,375,849 A | 3/1983 | Hanifl |
| 4,420,168 A | 12/1983 | Dewing |
| 4,466,538 A | 8/1984 | Gianni |
| 4,488,643 A | 12/1984 | Pepper |
| 4,494,652 A | 1/1985 | Nelson et al. |
| 4,502,606 A | 3/1985 | Shillington et al. |
| 4,520,926 A | 6/1985 | Nelson |
| 4,576,281 A | 3/1986 | Kirksey |
| 4,580,688 A | 4/1986 | Harris et al. |
| 4,600,112 A | 7/1986 | Shillington et al. |
| 4,637,545 A | 1/1987 | Stewart |
| 4,657,139 A | 4/1987 | Hanifl et al. |
| D292,037 S | 9/1987 | Hanifl |
| D292,777 S | 11/1987 | Shillington et al. |
| 4,715,498 A | 12/1987 | Hanifl |
| 4,736,860 A | 4/1988 | Bemis |
| 4,765,548 A | 8/1988 | Sing |
| 4,779,728 A * | 10/1988 | Hanifl .................. A61B 50/362 220/908 |
| 4,809,850 A * | 3/1989 | Laible .................. A61B 50/362 220/908 |
| 4,842,138 A | 6/1989 | Sandel et al. |
| D302,291 S | 7/1989 | Heubel et al. |
| 4,863,057 A | 9/1989 | Hanifl et al. |
| 4,867,309 A | 9/1989 | Germain |
| 4,869,366 A | 9/1989 | Bruno |
| D304,109 S | 10/1989 | Hanifl |
| 4,874,103 A | 10/1989 | Quisenberry et al. |
| 4,877,150 A | 10/1989 | Otto et al. |
| 4,883,189 A | 11/1989 | Lobbert |
| 4,886,164 A | 12/1989 | Stein et al. |
| 4,892,191 A | 1/1990 | Nakamura |
| 4,903,832 A | 2/1990 | Stewart |
| D306,509 S | 3/1990 | Hanifl et al. |
| 4,911,294 A | 3/1990 | Russo et al. |
| 4,913,309 A | 4/1990 | Fink |
| D307,841 S | 5/1990 | Hanifl et al. |
| 4,930,631 A | 6/1990 | Bruno |
| RE33,413 E | 10/1990 | Hanifl |
| D311,334 S | 10/1990 | Flynn et al. |
| 4,972,950 A | 11/1990 | Shillington |
| 4,984,686 A | 1/1991 | Shillington |
| 4,995,871 A | 2/1991 | Sasaki et al. |
| 4,997,103 A | 3/1991 | Daly |
| 5,005,729 A | 4/1991 | Hollman |
| 5,014,874 A | 5/1991 | Kitsos et al. |
| 5,024,326 A | 6/1991 | Sandel et al. |
| 5,024,327 A | 6/1991 | Shillington |
| 5,038,935 A | 8/1991 | Wenkman et al. |
| 5,046,613 A | 9/1991 | Baudry et al. |
| 5,048,712 A | 9/1991 | Wolters |
| 5,058,764 A | 10/1991 | Gaba |
| 5,062,828 A | 11/1991 | Waltz |
| 5,065,939 A | 11/1991 | Boothe et al. |
| 5,067,949 A | 11/1991 | Freundlich et al. |
| 5,076,429 A | 12/1991 | Patrick et al. |
| 5,076,458 A | 12/1991 | Weiner et al. |
| 5,080,251 A | 1/1992 | Noack |
| 5,082,132 A | 1/1992 | Tsai |
| 5,090,564 A | 2/1992 | Chimienti |
| 5,092,462 A | 3/1992 | Sagstetter et al. |
| 5,094,358 A | 3/1992 | Serio, Sr. |
| 5,097,950 A | 3/1992 | Weiss et al. |
| 5,107,990 A | 4/1992 | Wicherski et al. |
| D326,753 S | 6/1992 | DeBusk |
| 5,127,522 A | 7/1992 | Ranford |
| D328,810 S | 8/1992 | Boothe et al. |
| 5,143,389 A | 9/1992 | Jonkers |
| 5,145,063 A | 9/1992 | Lee |
| 5,152,394 A | 10/1992 | Hughes |
| 5,154,345 A | 10/1992 | Shillington |
| 5,163,574 A | 11/1992 | Sosan |
| 5,165,563 A | 11/1992 | Mckendry |
| 5,167,193 A | 12/1992 | Withers et al. |
| D332,680 S | 1/1993 | Ramirez |
| D332,852 S | 1/1993 | Delmerico |
| 5,176,256 A | 1/1993 | Sawaya |
| 5,178,322 A * | 1/1993 | Shillington ............. B65F 1/141 220/264 |
| 5,183,156 A | 2/1993 | Bruno |
| 5,184,720 A | 2/1993 | Packer et al. |
| 5,188,598 A | 2/1993 | Thead et al. |
| 5,193,678 A | 3/1993 | Janocik et al. |
| 5,195,635 A | 3/1993 | Cornwell |
| 5,195,649 A | 3/1993 | Wolters |
| 5,199,973 A | 4/1993 | Funk, Sr. |
| 5,201,417 A | 4/1993 | Outlaw, III |
| 5,201,418 A | 4/1993 | Hanlon |
| 5,230,525 A | 7/1993 | Delmerico et al. |
| 5,235,795 A | 8/1993 | Debusk |
| 5,240,108 A | 8/1993 | Tonna |
| 5,242,074 A | 9/1993 | Conaway et al. |
| D341,237 S | 11/1993 | Debusk |
| 5,273,161 A | 12/1993 | Sagstetter |
| 5,273,221 A | 12/1993 | Mccarthy |
| 5,275,280 A | 1/1994 | Everhart |
| 5,281,391 A | 1/1994 | Hanson et al. |
| 5,322,164 A | 6/1994 | Richardson et al. |
| 5,323,901 A | 6/1994 | Outlaw, III |
| 5,323,902 A | 6/1994 | Palmer et al. |
| 5,337,911 A | 8/1994 | Holub |
| 5,346,086 A | 9/1994 | Harris |
| 5,348,222 A | 9/1994 | Patey |
| 5,348,549 A | 9/1994 | Brown et al. |
| D351,906 S | 10/1994 | Marsh |
| 5,354,023 A | 10/1994 | Meeks |
| D352,350 S | 11/1994 | Rambo et al. |
| 5,372,271 A | 12/1994 | Miller et al. |
| 5,385,105 A | 1/1995 | Withers et al. |
| 5,386,910 A | 2/1995 | Liss |
| 5,387,735 A | 2/1995 | Ponsi et al. |
| 5,395,008 A | 3/1995 | Bemis et al. |
| 5,402,887 A | 4/1995 | Shillington |
| 5,409,113 A | 4/1995 | Richardson et al. |
| D358,240 S | 5/1995 | Mosior |
| 5,413,243 A | 5/1995 | Bemis et al. |
| 5,415,315 A | 5/1995 | Ramirez |
| 5,417,659 A | 5/1995 | Gaba |
| 5,419,435 A | 5/1995 | Perzan et al. |
| D360,062 S | 7/1995 | Mosior |
| 5,433,412 A | 7/1995 | Watt et al. |
| D362,502 S | 9/1995 | Anderson et al. |
| 5,458,072 A | 10/1995 | Hughes et al. |
| 5,465,841 A | 11/1995 | Wilson et al. |
| 5,474,180 A | 12/1995 | Robinson et al. |
| 5,474,181 A | 12/1995 | Shillington et al. |
| 5,474,201 A | 12/1995 | Liu |
| 5,474,341 A | 12/1995 | Putman et al. |
| 5,494,158 A | 2/1996 | Erickson |
| 5,494,186 A | 2/1996 | Marsh |
| 5,495,941 A | 3/1996 | Leonard |
| 5,507,408 A | 4/1996 | Mosior et al. |
| 5,531,346 A | 7/1996 | Mosior |
| 5,531,348 A | 7/1996 | Baker et al. |
| 5,538,158 A | 7/1996 | Prout et al. |
| 5,560,512 A | 10/1996 | Hahn |
| 5,570,547 A | 11/1996 | Webb et al. |
| 5,570,783 A | 11/1996 | Thorne et al. |
| 5,582,322 A | 12/1996 | Prout et al. |
| 5,603,404 A | 2/1997 | Nazare et al. |

(56) References Cited

U.S. PATENT DOCUMENTS

| | | |
|---|---|---|
| 5,605,245 A | 2/1997 | Bemis et al. |
| 5,630,506 A | 5/1997 | Thorne et al. |
| 5,647,502 A | 7/1997 | Marsh |
| 5,651,231 A | 7/1997 | Garland |
| 5,659,247 A | 8/1997 | Clements |
| 5,671,859 A | 9/1997 | Sheu et al. |
| D385,349 S | 10/1997 | Mosior et al. |
| D385,626 S | 10/1997 | Mosior et al. |
| 5,673,811 A | 10/1997 | Dickinson et al. |
| 5,690,242 A | 11/1997 | Campbell, Jr. |
| D388,577 S | 12/1997 | Rehrig et al. |
| 5,724,226 A | 3/1998 | Ruch et al. |
| 5,730,451 A | 3/1998 | Walker |
| D393,334 S | 4/1998 | Presnell et al. |
| 5,740,909 A | 4/1998 | Nazare et al. |
| 5,765,339 A | 6/1998 | Garland |
| 5,769,006 A | 6/1998 | Allaer |
| D403,241 S | 12/1998 | Nask et al. |
| 5,848,692 A | 12/1998 | Thorne et al. |
| D404,483 S | 1/1999 | Harwood et al. |
| 5,879,337 A | 3/1999 | Kuracina et al. |
| 5,890,615 A | 4/1999 | Petras |
| 5,899,468 A | 5/1999 | Apps et al. |
| 5,901,872 A | 5/1999 | Zollinhofer et al. |
| 5,901,874 A | 5/1999 | Deters |
| D411,008 S | 6/1999 | Gaba et al. |
| 5,918,762 A | 7/1999 | Gaba et al. |
| 5,947,285 A | 9/1999 | Gaba et al. |
| D414,864 S | 10/1999 | Gaba et al. |
| D415,273 S | 10/1999 | Gaba et al. |
| 5,967,317 A | 10/1999 | Wright |
| 5,984,137 A | 11/1999 | Grosjean |
| 6,001,080 A | 12/1999 | Kuracina et al. |
| 6,010,024 A | 1/2000 | Wang |
| D421,122 S | 2/2000 | Gaba et al. |
| 6,053,354 A | 4/2000 | Niemeyer |
| 6,062,001 A | 5/2000 | Kunik |
| 6,070,751 A | 6/2000 | Mejias |
| D429,864 S | 8/2000 | Schmidt |
| D431,079 S | 9/2000 | Crawford |
| 6,120,743 A | 9/2000 | Papari |
| 6,138,558 A | 10/2000 | Harrington |
| D438,964 S | 3/2001 | Gaba et al. |
| 6,202,922 B1 | 3/2001 | Phillips et al. |
| 6,250,465 B1 | 6/2001 | Daniels et al. |
| D445,228 S | 7/2001 | Apps et al. |
| 6,253,916 B1 | 7/2001 | Bickel |
| D447,233 S | 8/2001 | Bickel et al. |
| 6,283,909 B1 | 9/2001 | Sharp |
| 6,286,675 B1 | 9/2001 | Schmidt |
| D451,195 S | 11/2001 | Daniels et al. |
| D451,255 S | 11/2001 | Schmidt |
| D452,944 S | 1/2002 | Schmidt |
| 6,341,438 B1 | 1/2002 | Sianos |
| 6,435,729 B1 | 8/2002 | Thevenod et al. |
| 6,443,929 B1 | 9/2002 | Kuracina et al. |
| 6,460,453 B1 | 10/2002 | Frauenfeld |
| 6,540,098 B1 | 4/2003 | Jarvis et al. |
| 6,561,352 B2 | 5/2003 | Sherman et al. |
| D478,663 S | 8/2003 | Moats et al. |
| D478,664 S | 8/2003 | Moats et al. |
| D478,701 S | 8/2003 | Panek, Jr. |
| 6,612,457 B1 | 9/2003 | Caron |
| 6,623,316 B1 | 9/2003 | Wu |
| 6,626,316 B2 | 9/2003 | Yang |
| 6,626,321 B2 | 9/2003 | Jaeger |
| 6,651,992 B1 | 11/2003 | Smith, Sr. |
| D485,906 S | 1/2004 | Danssaert et al. |
| 6,691,867 B1 | 2/2004 | Bickel et al. |
| 6,712,207 B2 | 3/2004 | Panek, Jr. et al. |
| 6,722,672 B2 | 4/2004 | Cates et al. |
| 6,761,283 B1 | 7/2004 | Gilliam et al. |
| 6,889,831 B2 | 5/2005 | Pike |
| D518,173 S | 3/2006 | Coates |
| D531,309 S | 10/2006 | Bennett |
| 7,114,629 B2 | 10/2006 | Panek, Jr. |
| 7,119,689 B2 | 10/2006 | Mallett et al. |
| 7,123,150 B2 | 10/2006 | Mallett et al. |
| 7,126,480 B2 | 10/2006 | Mallett et al. |
| 7,138,918 B2 | 11/2006 | Mallett et al. |
| D538,499 S | 3/2007 | Schmidt |
| 7,192,037 B1 | 3/2007 | Peña |
| D545,521 S | 6/2007 | Titas et al. |
| 7,243,792 B2 | 7/2007 | Panek, Jr. et al. |
| 7,275,645 B2 | 10/2007 | Mallett et al. |
| 7,296,688 B2 | 11/2007 | Mallett et al. |
| D556,545 S | 12/2007 | Titas et al. |
| 7,303,080 B2 | 12/2007 | Mallett et al. |
| 7,303,081 B2 | 12/2007 | Mallett et al. |
| 7,303,082 B2 | 12/2007 | Mallett et al. |
| 7,311,207 B2 | 12/2007 | Mallett et al. |
| D560,489 S | 1/2008 | Satnick et al. |
| 7,318,529 B2 | 1/2008 | Mallett et al. |
| 7,341,147 B2 | 3/2008 | Mallett et al. |
| 7,364,049 B2 | 4/2008 | Panek, Jr. |
| D569,074 S | 5/2008 | Irwin et al. |
| 7,383,195 B2 | 6/2008 | Mallett et al. |
| 7,392,903 B2 | 7/2008 | Jolley et al. |
| D575,061 S | 8/2008 | Titas et al. |
| 7,445,116 B2 | 11/2008 | Dansaert et al. |
| 7,454,358 B2 | 11/2008 | Mallett et al. |
| 7,483,837 B2 | 1/2009 | Mallett et al. |
| 7,487,100 B2 | 2/2009 | Mallett et al. |
| 7,513,363 B2 | 4/2009 | Brown et al. |
| 7,516,844 B2 | 4/2009 | Erickson et al. |
| D591,859 S | 5/2009 | Stark et al. |
| 7,533,028 B2 | 5/2009 | Mallett et al. |
| 7,533,029 B2 | 5/2009 | Mallett et al. |
| 7,534,392 B1 | 5/2009 | Kodis |
| 7,534,405 B1 | 5/2009 | Kodis |
| 7,562,025 B2 | 7/2009 | Mallett et al. |
| 7,565,299 B2 | 7/2009 | Mallett et al. |
| 7,596,844 B2 | 10/2009 | Japuntich et al. |
| 7,597,681 B2 | 10/2009 | Sutton et al. |
| 7,600,638 B2 | 10/2009 | Finnestad et al. |
| 7,600,639 B2 | 10/2009 | Japuntich et al. |
| 7,617,113 B2 | 11/2009 | Mallett et al. |
| 7,620,559 B2 | 11/2009 | Mallett et al. |
| 7,660,724 B2 | 2/2010 | Mallett et al. |
| 7,664,656 B2 | 2/2010 | Mallett et al. |
| 7,694,811 B2 | 4/2010 | Brown et al. |
| 7,694,822 B2 | 4/2010 | Sullivan et al. |
| 7,699,247 B2 | 4/2010 | Kodis |
| 7,775,387 B2 | 8/2010 | Lipton et al. |
| 7,776,262 B1 | 8/2010 | Kodis |
| 7,784,167 B2 | 8/2010 | Panek, Jr. |
| 7,789,230 B2 | 9/2010 | Klein |
| 7,815,046 B2 | 10/2010 | Sansoucy et al. |
| 7,877,849 B2 | 2/2011 | Panek, Jr. et al. |
| 7,898,201 B2 | 3/2011 | Fisher et al. |
| 7,931,878 B2 | 4/2011 | Kodis |
| 7,937,814 B2 | 5/2011 | Voit |
| 7,970,722 B1 | 6/2011 | Owen et al. |
| 7,971,715 B1 | 7/2011 | Fernandes et al. |
| 7,980,408 B2 | 7/2011 | Japuntich et al. |
| 8,005,777 B1 | 8/2011 | Owen et al. |
| 8,038,025 B2 | 10/2011 | Stark et al. |
| 8,096,414 B2 | 1/2012 | Finnestad et al. |
| D655,061 S | 2/2012 | Scaturro |
| 8,113,349 B2 | 2/2012 | Sansoucy et al. |
| 8,160,988 B1 | 4/2012 | Owen et al. |
| 8,162,139 B2 | 4/2012 | Iske |
| 8,172,859 B2 | 5/2012 | Matsuno et al. |
| 8,195,328 B2 | 6/2012 | Mallett et al. |
| 8,201,323 B2 | 6/2012 | Miller et al. |
| 8,204,620 B2 | 6/2012 | Mallett et al. |
| 8,209,918 B2 | 7/2012 | Voit |
| 8,296,243 B2 | 10/2012 | Mallett et al. |
| 8,324,443 B2 | 12/2012 | Kunik et al. |
| 8,393,488 B2 | 3/2013 | Japuntich et al. |
| 8,584,885 B2 | 11/2013 | Finnestad et al. |
| 9,511,913 B2 * | 12/2016 | Brooks ................ B65F 1/1607 |
| 2002/0158068 A1 | 10/2002 | Panek |
| 2003/0213714 A1 | 11/2003 | Moats et al. |

(56) References Cited

U.S. PATENT DOCUMENTS

| | | | |
|---|---|---|---|
| 2004/0020927 | A1 | 2/2004 | Yang et al. |
| 2006/0070898 | A1 | 4/2006 | Dansaert et al. |
| 2009/0108007 | A1 | 4/2009 | Anderson et al. |
| 2011/0024414 | A1 | 2/2011 | Widmer |
| 2012/0024878 | A1 | 2/2012 | Kelly et al. |
| 2012/0037626 | A1 | 2/2012 | Finnestad |
| 2017/0107015 | A1* | 4/2017 | Reinhart ............ B65D 43/0214 |

FOREIGN PATENT DOCUMENTS

| | | |
|---|---|---|
| DE | 2740335 A1 | 3/1979 |
| DE | 3908186 A1 | 3/1990 |
| EP | 541339 A2 | 5/1993 |
| EP | 527938 B1 | 3/1996 |
| EP | 842641 A1 | 5/1998 |
| EP | 1447109 A2 | 8/2004 |
| EP | 1609432 A1 | 12/2005 |
| EP | 1709925 A1 | 10/2006 |
| EP | 2057958 A2 | 5/2009 |
| FR | 2730919 A1 | 8/1996 |
| FR | 2746931 A1 | 10/1997 |
| FR | 2759064 A1 | 8/1998 |
| FR | 2766799 A1 | 2/1999 |
| GB | 2040268 A | 8/1980 |
| GB | 2277247 A | 10/1994 |
| GB | 2388032 A | 11/2003 |
| GB | 2398225 A | 8/2004 |
| GB | 2447008 A | 9/2008 |
| NL | 1003928 C2 | 3/1998 |
| WO | 1988008399 A1 | 11/1988 |
| WO | 1991001920 A2 | 2/1991 |
| WO | 1991017095 A1 | 11/1991 |
| WO | 1991017099 A1 | 11/1991 |
| WO | 1993009039 A1 | 5/1993 |
| WO | 1994021538 A1 | 9/1994 |
| WO | 1995003076 A1 | 2/1995 |
| WO | 1995033417 A2 | 12/1995 |
| WO | 1996006024 A1 | 2/1996 |
| WO | 1996009228 A1 | 3/1996 |
| WO | 1996020880 A1 | 7/1996 |
| WO | 1996025894 A1 | 8/1996 |
| WO | 1996031414 A1 | 10/1996 |
| WO | 1997037413 A1 | 10/1997 |
| WO | 1998034855 A1 | 8/1998 |
| WO | 1998057869 A1 | 12/1998 |
| WO | 1999059659 A1 | 11/1999 |
| WO | 2000042938 A1 | 7/2000 |
| WO | 2003091710 A1 | 11/2003 |
| WO | 2005120610 A2 | 12/2005 |
| WO | 2006119247 A1 | 11/2006 |
| WO | 2007038133 A1 | 4/2007 |
| WO | 2008036218 A2 | 3/2008 |
| WO | 2009055661 A2 | 4/2009 |

* cited by examiner

SHARPS CONTAINER

RELATED APPLICATIONS

The present invention is a continuation of U.S. patent application Ser. No. 16/845,842 filed Apr. 10, 2020, now U.S. Pat. No. 11,559,369 issued Jan. 24, 2023, which is a continuation of U.S. patent application Ser. No. 16/436,920 filed Jun. 11, 2019, now U.S. Pat. No. 10,617,485 issued Apr. 14, 2020, which is a continuation of U.S. patent application Ser. No. 14/921,586 filed Oct. 23, 2015, now U.S. Pat. No. 10,321,968 issued Jun. 18, 2019, which applications are incorporated herein by reference in their entirety.

FIELD OF THE INVENTION

The present invention relates generally to containers for disposal of medical waste, and in particular to the disposal of contaminated items. The present invention may be a disposal system for use in a hospital or similar environment where contaminated items must be collected and disposed of without creating a hazard for patients or hospital personnel.

BACKGROUND OF THE INVENTION

In hospitals, clinics and similar institutions, contamination is of utmost concern. Disposable, single use patient-care products, which used to be the exception, are now the norm. Such hospital waste products might include surgical sharps, such as needles, syringes, scalpel blades, or the like, or might include gauzes, bandages, or sponges.

Various types of containers for hospital use have been developed for receiving medical waste in a surgical operating room, pre-op or post-op room, or a patient's room. These containers are particularly designed to protect the user of such containers, such as doctors, nurses, or other hospital personnel, from the hospital waste products that may be disposed therein.

The proximal disposal of sharps in patient rooms has spawned a host of specialized sharps disposal containers. These containers are primarily designed to allow for the easy disposal of sharps in a manner that does not require excess effort, exposure to the sharp portion of a device and in which the disposed of sharp cannot be subsequently accessed. In most instances, the disposal system consists of a non-disposable cabinet or support that is more or less permanently affixed to a room surface (usually affixed to the wall with some type of anchor) and a disposable container that fits within or is attached to the cabinet or support. Typically, the disposable container utilizes some type of door that prevents unobstructed access to the interior of the container, but allows relatively easy disposal of the sharp.

It is important to prevent the user of a sharps container from being accidentally cut or punctured by its contents. Furthermore, it is important to prevent access to the contents of the container during disposal thereof.

Sharps containers have commonly been provided with a relatively large circular opening through which sharps may be dropped in a vertical orientation for haphazard collection within the container. As the container fills, the user runs the risk of a previously inserted sharp protruding from the opening where it can stab the hand of the next operator inserting something into the container. Side walls may be constructed of relatively soft or thin-walled material which could be pierced by any one of the haphazardly arranged needles within the container thereby possibly exposing to infectious disease the next person brushing against the container. Other known sharps containers have a mailbox-like structure having a tilt pan which tips outwardly for receiving a sharp and which tips inwardly for depositing the sharp in the container. In this manner, the interior of the container is never completely open to the room and the sharp can be disposed of with one simple motion.

However, previous designs have been subject to jamming, improper function and manufacturing difficulties. For example, previous designs included lids with multiple distinct parts. In some examples, these parts may be ultrasonically welded together. This creates extra manufacturing steps as well as unnecessarily using more plastic.

DETAILED DESCRIPTION

Figure 1:
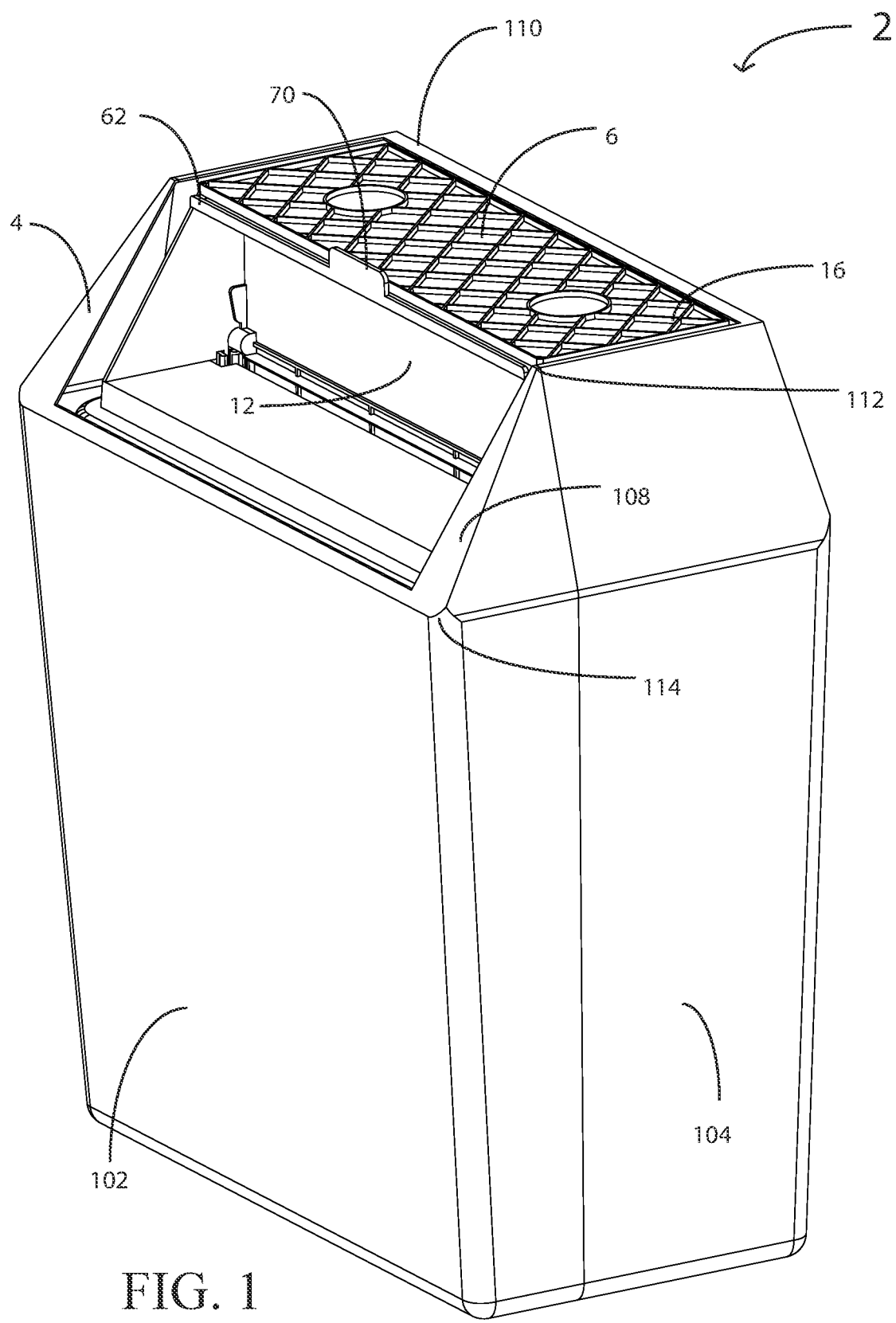
FIG. 1 is a side perspective view of a sharps disposal system including a permanent exterior cabinet and disposable interior container.
Figure 2:
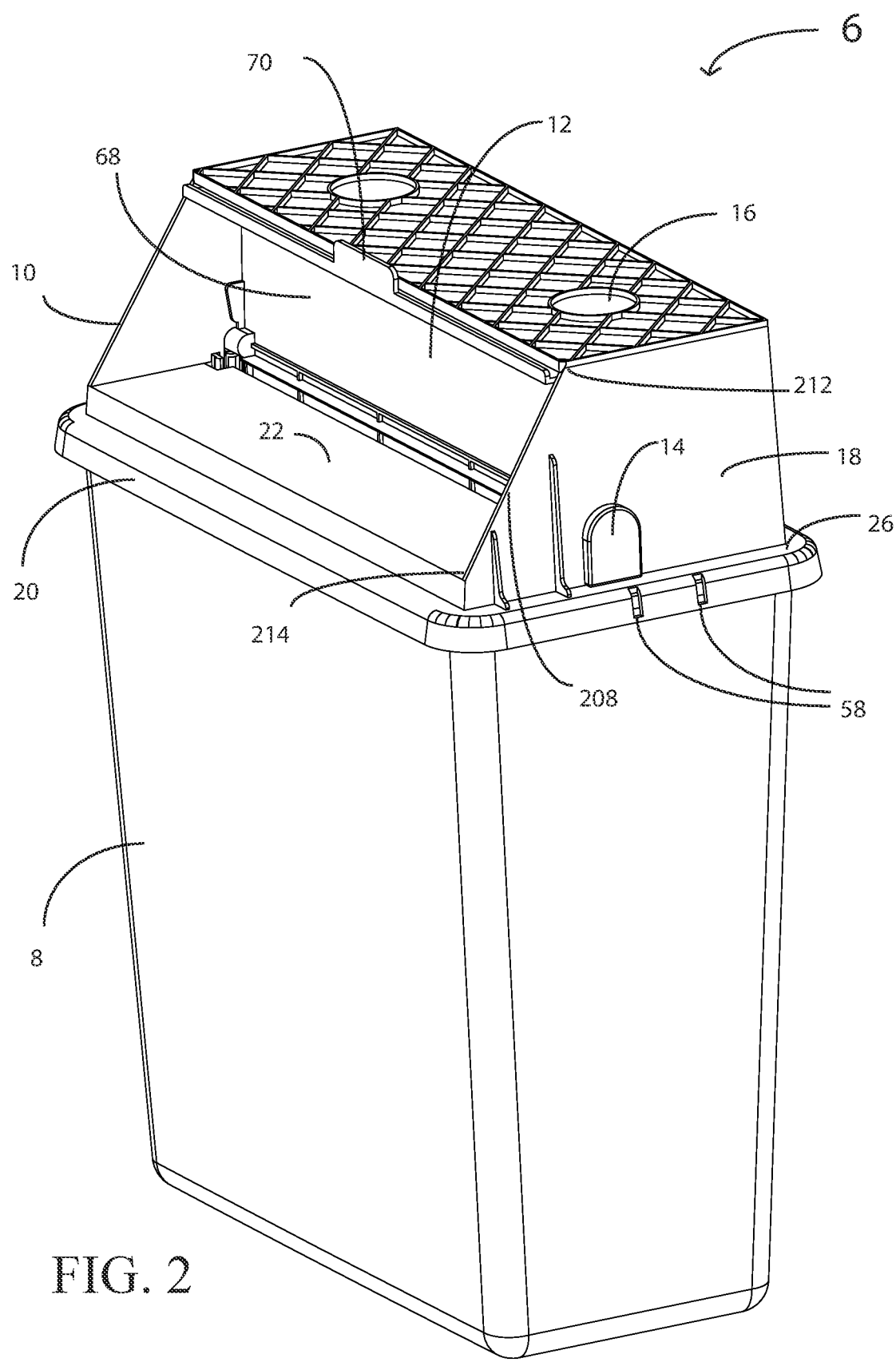
FIG. 2 is a side perspective view of the disposable interior container with the closure flap in a closed position.

With reference to FIGS. 1-2, the disposal system 2 of the present invention includes a locking exterior cabinet 4 that may be wall mounted and a disposable container 6 that is placed within the cabinet 4. For example, as shown in FIG. 1, the cabinet 4 includes a bottom wall, rear wall 110, opposite upstanding side walls 104 and a front wall 102. The front wall 102 may be hinged to the side wall 104 or to the bottom wall such that the front wall can be swung open to remove the disposable container 6 from the cabinet 4. The front wall 102 or corresponding side wall 104 may include a locking mechanism (not shown) for securely locking a disposable container 6 into the cabinet 4. The locking mechanism may comprise a locking tab or latch, or it may include a keyed lock.

The cabinet 4 may be secured to a wall, desk, table or other surface. The securing mechanism may consist of screws or other fasteners inserted through the cabinet into the surface that are only accessible when the cabinet 4 is opened and the container 6 is removed. In this way, the cabinet could only be removed from the surface by someone with access to a cabinet key. Alternatively, an exterior frame, locking tabs or other mechanism may be provided to attach the cabinet to the surface.

As further shown in FIG. 1, embodiments of the cabinet 4 may not include a top wall. Rather, the cabinet side walls 104 and rear wall 110 may extend to and generally parallel to or below a top surface 16 of the container 6. Alternatively, the cabinet may include a top wall that is dimensioned so as not to interfere with movement of a closure flap 12 of the container 6. The front wall 102 of the cabinet 4 may have an angled or sloped portion 108. The sloped portion 108 may be angled such that the top end portion 112 of the sloped portion 108 aligns generally with an upper portion 62 of the closure flap 12 when the closure flap 12 is in a closed and locked position, and the bottom end portion 114 of the sloped portion 108 aligns below an upper portion 62 of the closure flap 12 when the closure flap is in an open position.

Figure 3:
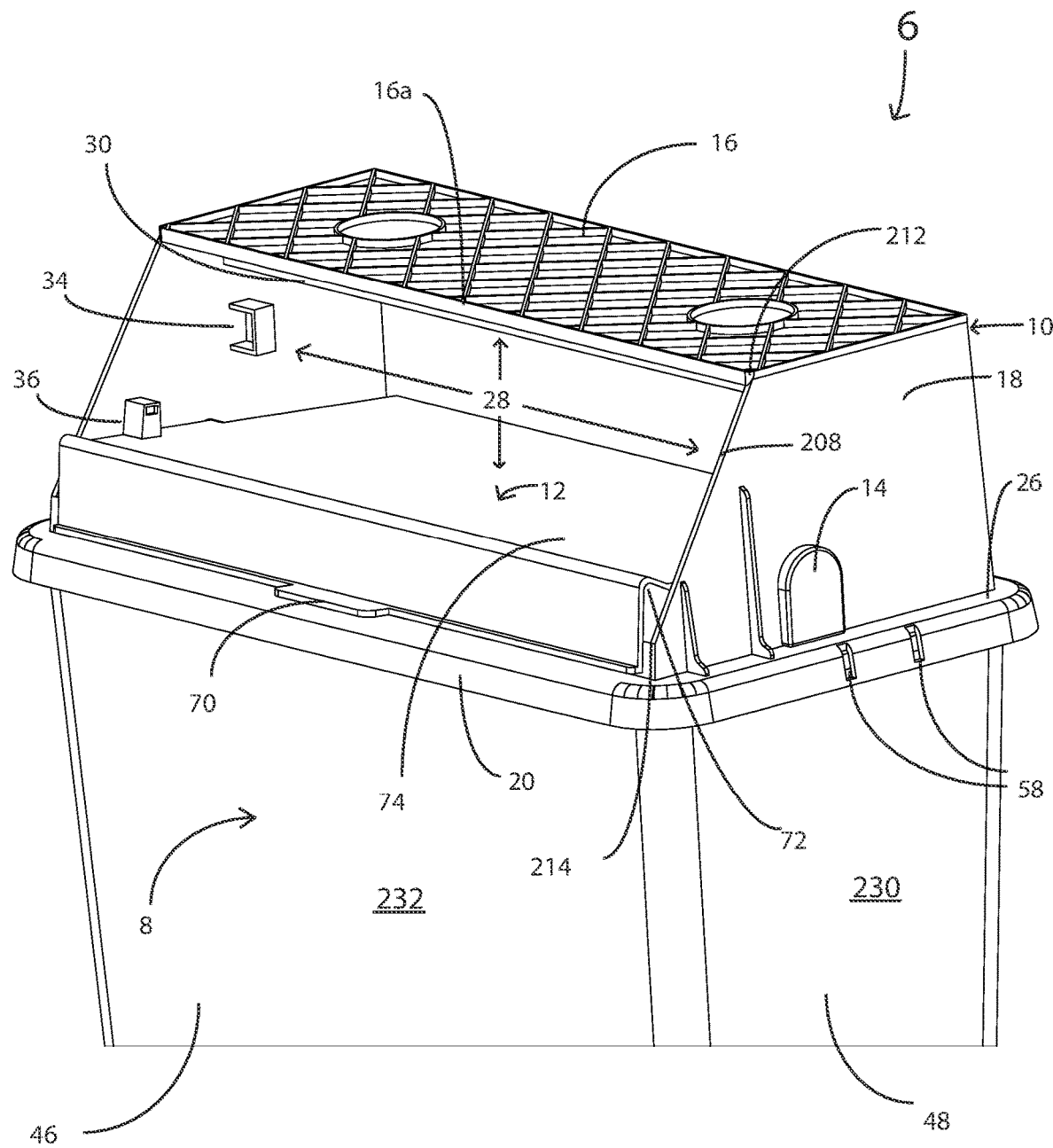
FIG. 3 is a front perspective view of the disposable interior container with the closure flap in an opened position.
Figure 4:
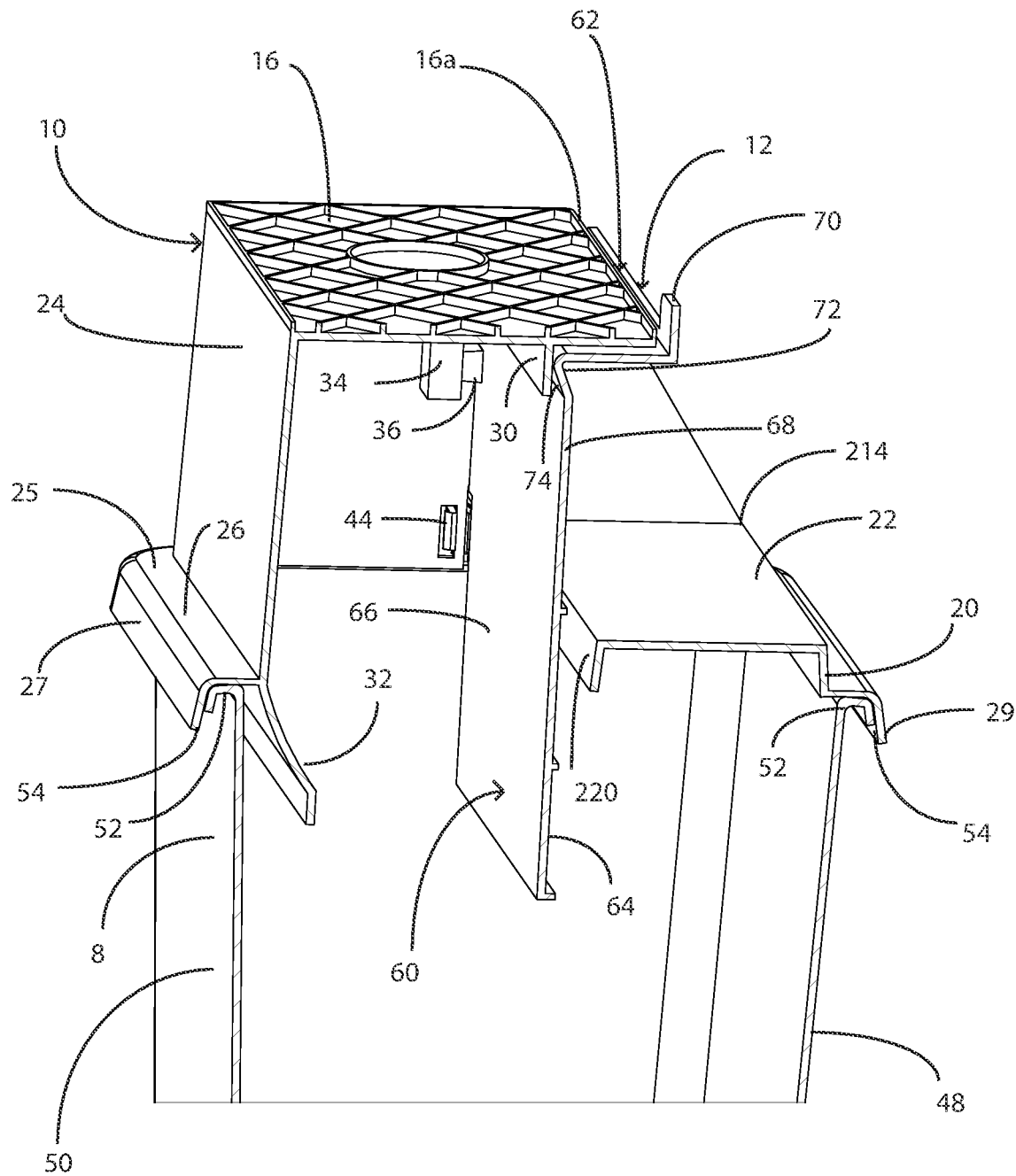
FIG. 4 is a side cut-away view of the interior of the disposable container with the closure flap in a closed and locked position.

As show in FIGS. 2-4, the disposable container 6 is preferably formed of four component parts including an open topped receptacle 8 for receiving medical waste, a snap fit lid 10, a pivotal closure flap 12 and a plurality of snap fit covers 14. The front portions of the lid side wall 18 may include a sloped portion 208 that generally corresponds with the sloped portion 108 of the cabinet front wall 102. Similarly, the sloped portion 208 may be angled such that the top portion 212 of the sloped portion 208 aligns generally with an upper portion 62 of the closure flap 12 when the closure flap 12 is in a closed and locked position, and the bottom end portion 214 of the sloped portion 208 aligns below an upper portion 62 of the closure flap 12 when the closure flap 12 is in an open position. The front shelf 22 provides a deck upon which the closure flap 12 may rest when in the open position.

As shown in FIGS. 3-4, the lid 10 includes an upper wall 16, side walls 18, a front wall 20, a front shelf 22, a rear wall 24, and a skirt 26 extending around the lower portions of the lid 10 side and rear walls 18, 24. Located in spaced relation between the front shelf 22, the front portion 16a of the upper wall 16 and front portion of the side walls 18, an elongated opening 28 is provided for receiving the closure flap 12 which is pivotally operable between a normal closed position, a fully opened position and a permanently closed and locked position. The closure flap is sized such that when is in the normal closed position, the lower portion 60 of the closure flap 12 extends into the receptacle 8 in spaced relation with the bottom wall (not shown) of the receptacle 8 and the upper portion 62 of the closure flap 12 extends above the lid upper wall 16. Still further, the closure flap is sized such that when in the open position, the lower portion 60 of the closure flap 12 sweeps immediately adjacent to the interior rear wall 24 of the lid 10 and the detent 72 of the upper portion of the closure flap approximately corresponds with the portion of the lid 10 where the front wall 20 and the front shelf 22 meet.

Figure 11:
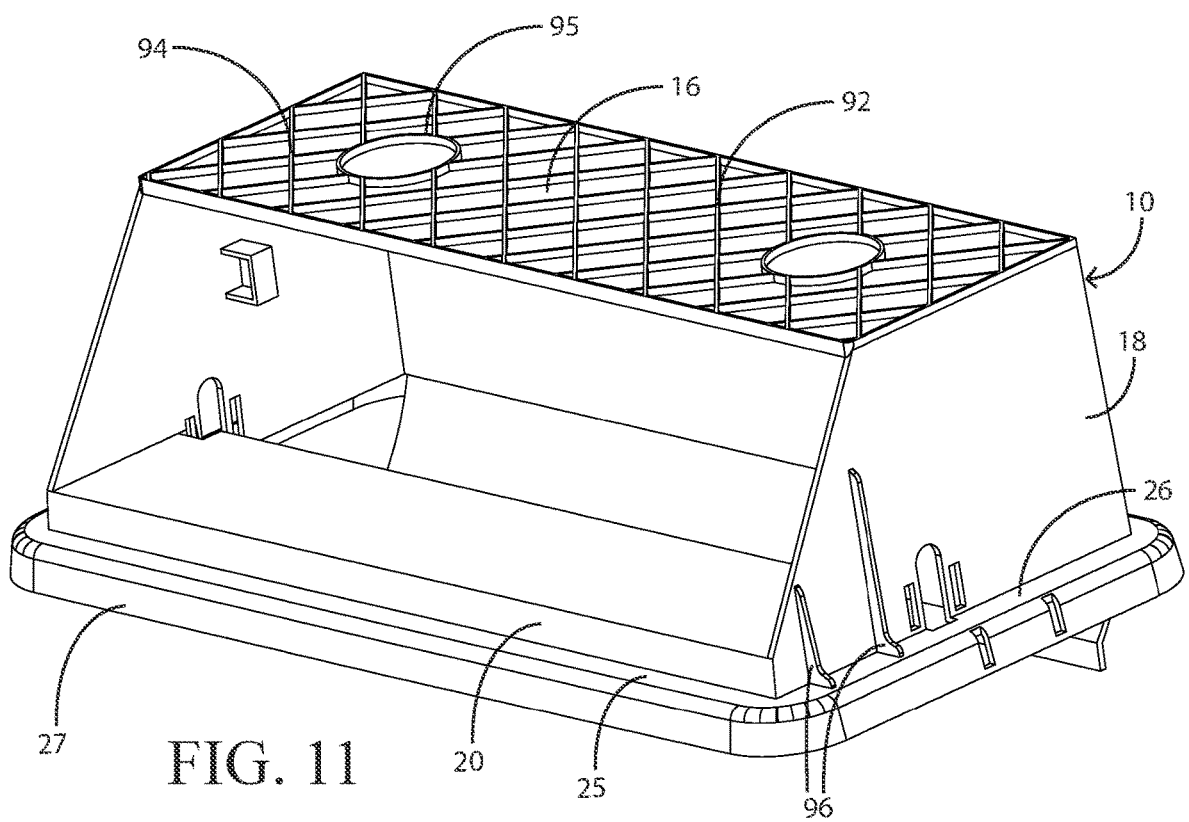
FIG. 11 is a perspective view of a lid of a disposable interior container.

The upper wall 16 of the lid 10 may have a generally planar and smooth surface as illustrated in FIG. 3. Alternatively, as shown in FIG. 11, embodiments of the lid 10 may include an upper wall 16 that incorporates one or more decorative or structural features. For example, the upper wall 16 may incorporate ribs 92 that increase the structural rigidity of the upper wall. These ribs may be formed in a cross-hatch pattern 94 or a circular pattern 95, or some combination of these or other patterns as may be appropriate to enhance the structure and/or aesthetics of the upper wall.

Additionally, the lid 10 may incorporate ribs 96 that bridge the gap between the side wall 18 and the lid skirt 26 in order to provide additional structural integrity to the lid.

Figure 12:
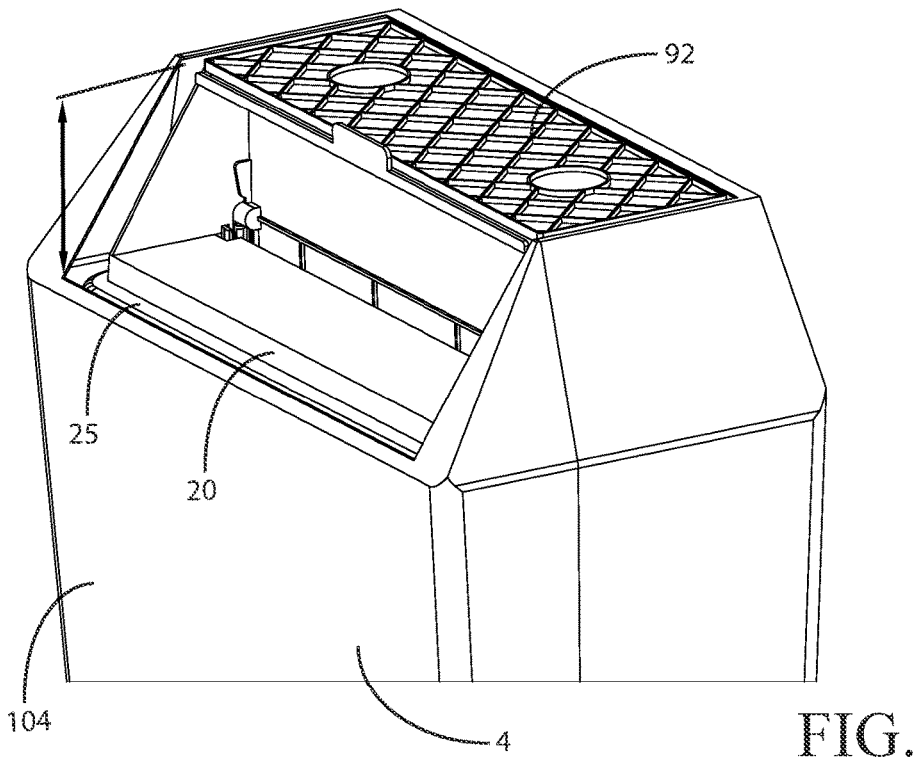
FIG. 12 is a perspective view of a sharps disposal system including a permanent exterior cabinet and disposable interior container.

As shown in FIG. 4, the skirt 26 may include a horizontal portion 25 that extends from the lid side 18 and rear walls 24. The skirt may also include a vertical portion 27 that extends below a flange 52 of the receptacle 8. In some embodiments, as illustrated in FIG. 4, the skirt 26 may not include a horizontal portion adjacent to the front wall 20. And the skirt 26 may generally vertically from the edge of the front shelf 22 to a lower edge 29 of the skirt. Alternatively, as illustrated in FIGS. 11-12, embodiments of the lid 10 may include a skirt horizontal portion 25 that extends adjacent to the front wall 20 in addition to the side walls 18 and rear wall. This horizontal portion 25 may be positioned such that it accommodates the geometry of the front wall 104 of the cabinet 4. For example, a top edge of the cabinet front wall 104 may include a lip that extends partially over the horizontal portion of the skirt 26.

Figure 5:
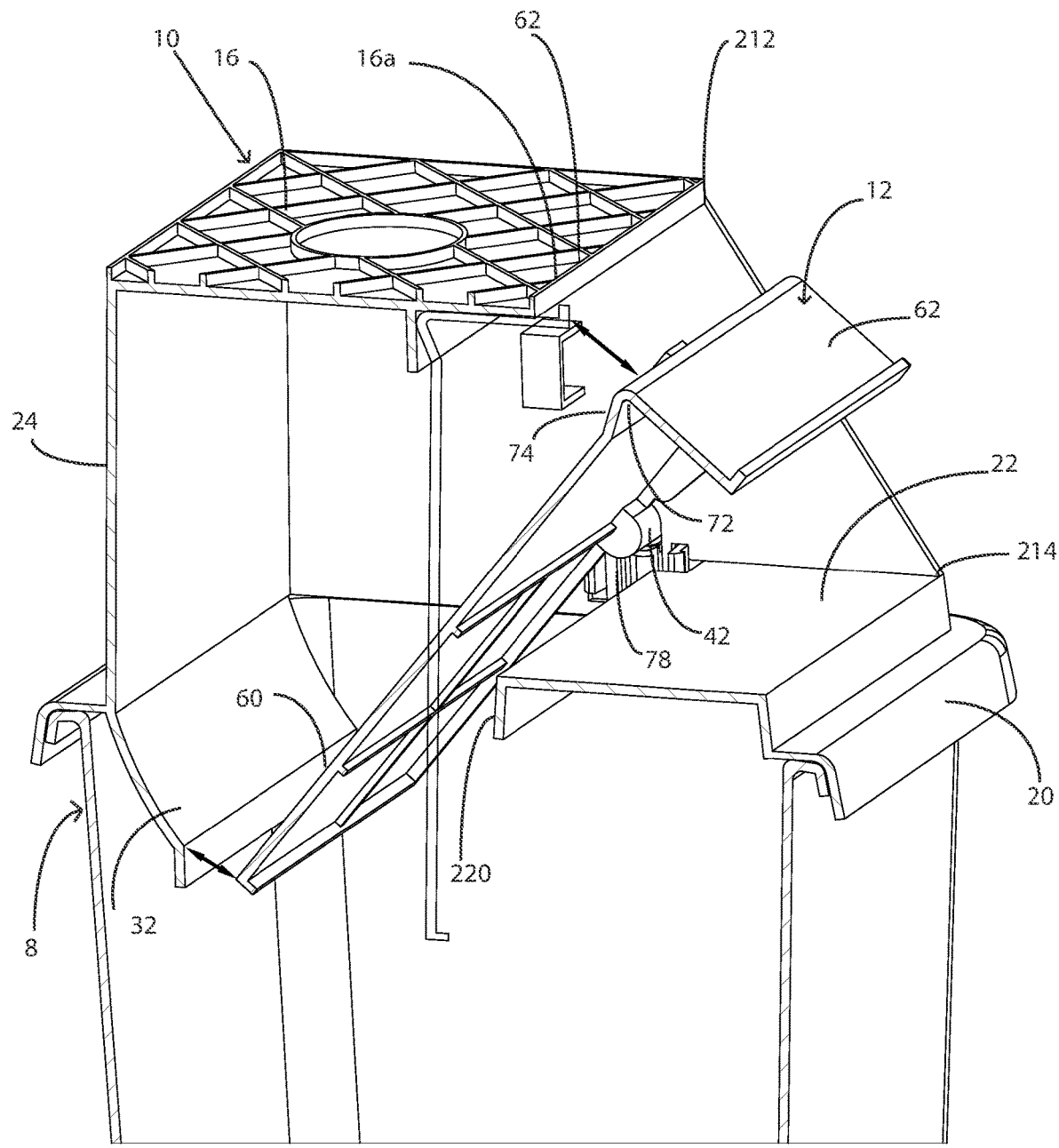
FIG. 5 is a side cut-away view of the interior of the disposable container with the closure flap in a partially open position.
Figure 6:
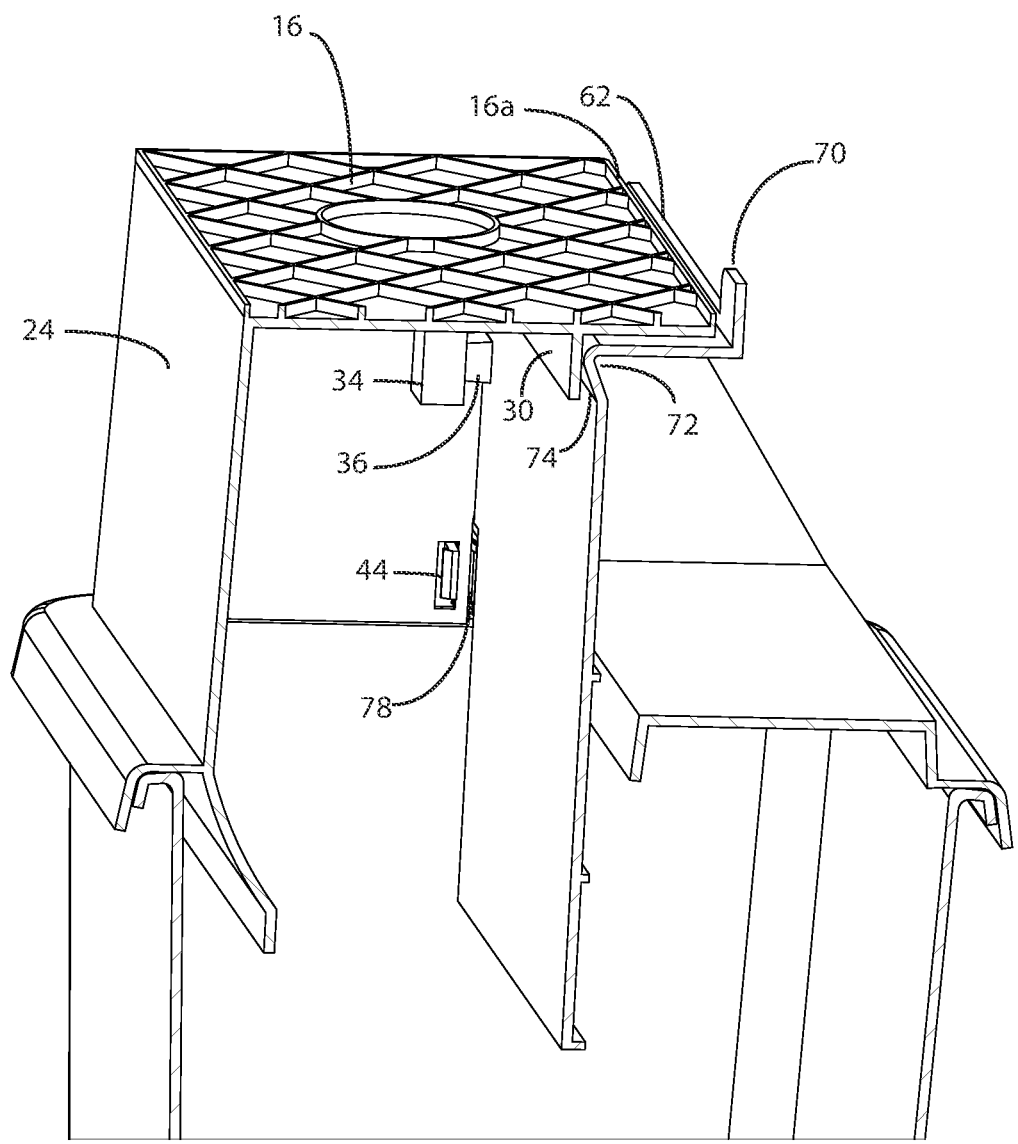
FIG. 6 is a side cut-away view of the interior of the disposable container with the closure flap in a closed and permanently locked position.

Turning to the interior surfaces of the lid 10, a plurality of features are provided to protect the user from accidental exposure to medical waste located within the receptacle 8. As shown in FIGS. 4-7 the front portion 16a of upper wall 16 interior, in spaced relation with the opening 28, includes a downward projection 30. As shown in FIGS. 4 and 5, the rear wall 24 interior includes a fixed cowl 32 which extends downwardly into the receptacle 8 to assist in guiding horizontally disposed sharps placed on the closure flap 12 into the receptacle 8. The projection 30 and the cowl 32 restrict access into the interior of the container 6 when the closure flap 12 is in a fully open position by constricting access within the area that is the opening 28. The relative spacing of the front shelf 22, the downward projection 30 and the cowl 32 define a limited opening 28 which restricts access to the interior of the container 6. The relative spacing of these features are dimensioned so that access to the interior of the container 6 is inhibited to the extent that it is difficult or impossible for an adult human hand to pass through the opening 28. Still further, once the closure flap 12 is locked in a fully closed position, if the closure flap 12 is pried away from the front portion 16a of the lid upper wall 16 in an attempt to gain access to the interior of the container 6, the projection 30 offers a further safety feature by restricting access to the interior of the container.

The front shelf 22 includes a front portion that aligns with the front wall 20 and a rear portion that includes a projection 220, which is directed downward into the interior of the receptacle 8. When the closure flap 12 is in a closed position, the medial portion of the closure flap rests against the downward projection 220. As with other lid interior features, downward projection 220 assists in restricting access into the interior of the contain 6 by providing structural support to the front shelf 22, as well as offers a further safety feature by restricting access to the interior of the container 6 in the event an attempt to pry open the closure flap 12 is made in an attempt to gain access to the interior of the container Additionally, in spaced relation with the interior upper wall 16 the interior side walls 18 are provided a plurality of slots 34 through which hooks 36 of the closure flap 12 are inserted to provide permanent closure of the container 6 for transport and disposal. Once the hooks 36 pass through the slots 34, movement of the closure flap 12 is blocked so that force applied against the closure flap 12 will not move the closure flap 12 from a closed position to an open position.

Figure 8:
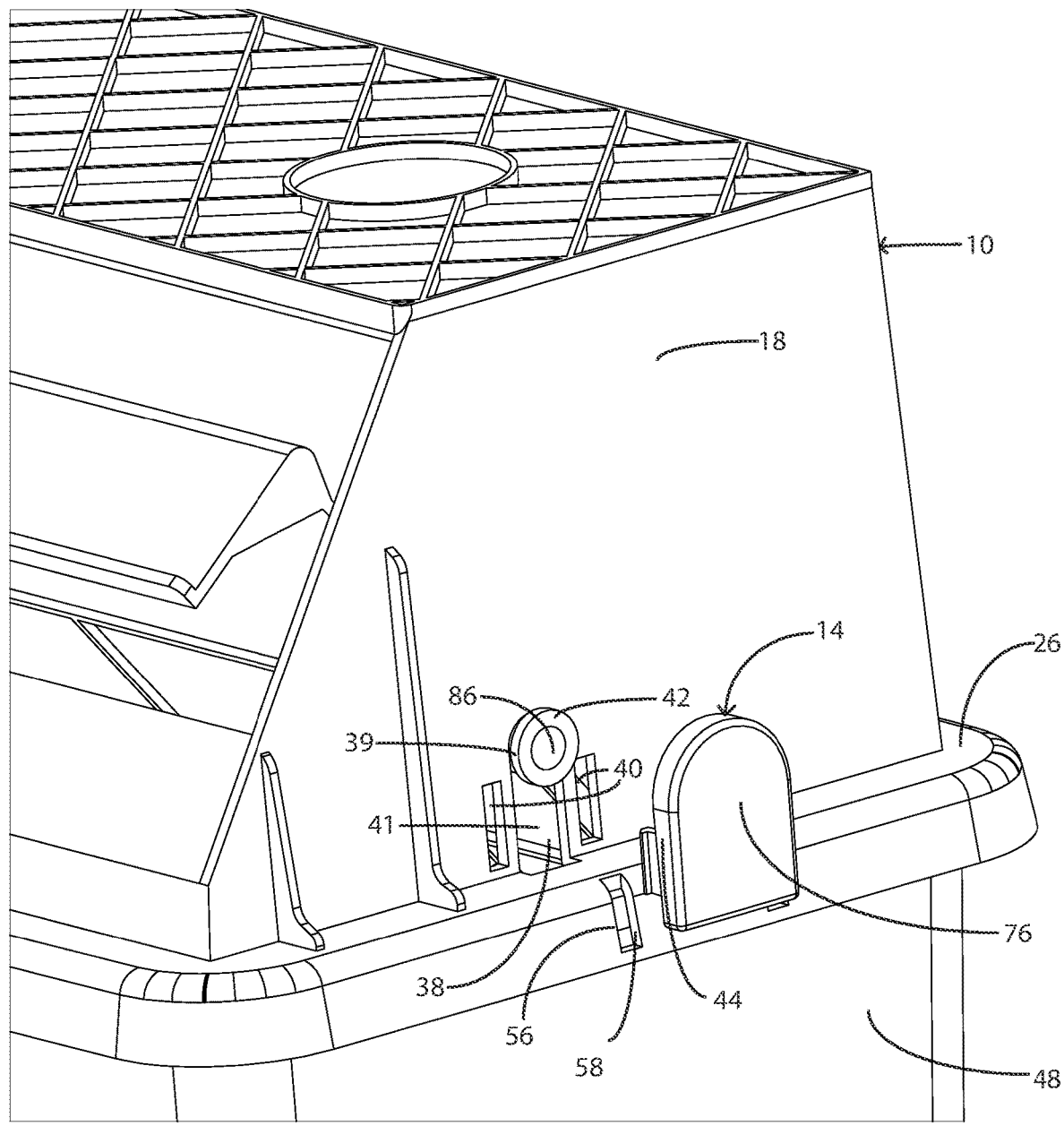
FIG. 8 is a partially exploded side perspective view of the lid of the disposable container.

As shown in FIG. 8, the lid 10 may also include an opening 38 through which an axial hub 42 of the closure flap 12 may be inserted. In addition, the lid may include openings 40 through which locking tabs 44 of the snap fit cover 14 extend, as discussed in greater detail below.

The receptacle 8 includes a bottom wall, front wall 46, rear wall 48 and side walls 50. As shown in FIG. 4, the upper portions of the receptacle 8 front, rear and side walls, 46, 48, 50 include a flange 52 that extends outwardly and downwardly from the top edge of the side walls. The flange is adapted to receive corresponding inwardly extending locking fingers 54 of the lid skirt 26 to provide a permanent snap fit connection between the lid 10 and receptacle 8.

Figure 9:
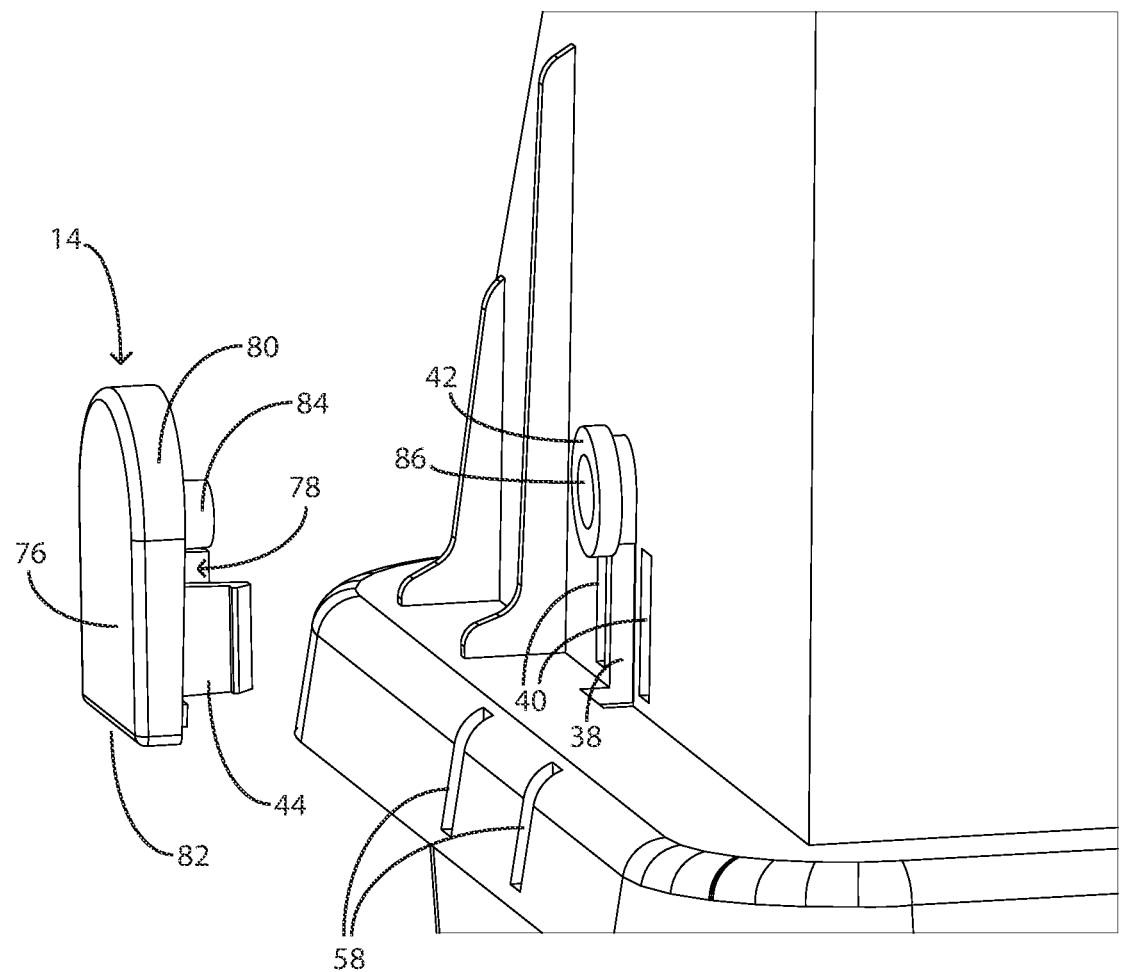
FIG. 9 is an exploded side perspective view of the lid and component parts of the disposable container.

As shown in FIGS. 8-9, the upper edges of the receptacle 8 side walls 48 may include locking fingers 56 that are inserted into through openings 58 located on the lid 10 side wall skirt 26 permanent provide a snap fit connection between the receptacle 8 and lid 10.

Additional embodiments of the disposal system may include viewing ports in the one or more of the front 102 and side 104 walls of the cabinet 4. These view ports correspond to view ports 230, 232 (FIG. 3) that may be located in the front 46 and side 50 walls of the receptacle 8. The viewing ports permit a user to view the contents of the system and determine empty/full status prior to attempted use.

Figure 7:
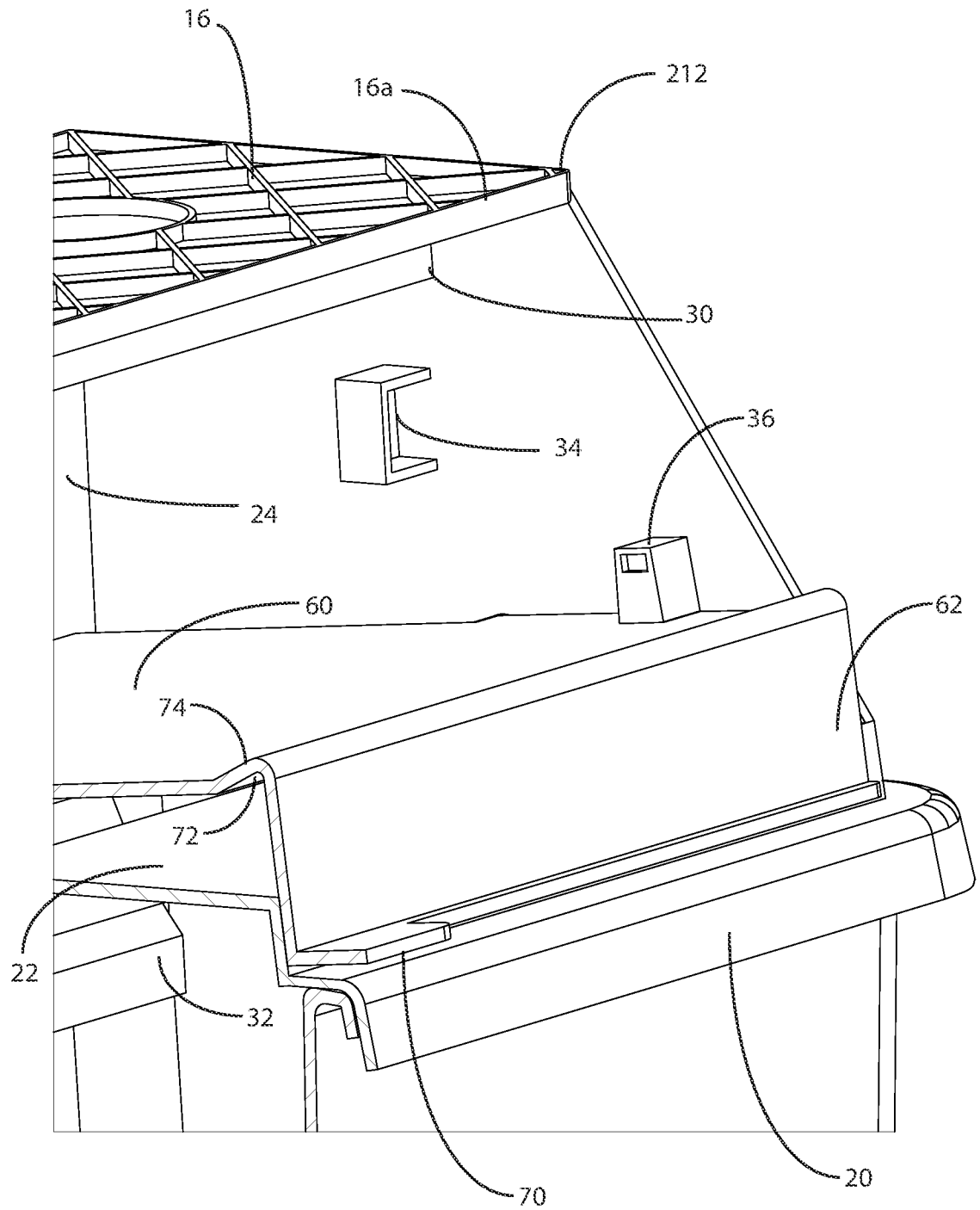
FIG. 7 is a side cut-away view of the interior of the disposable container with the closure flap in a completely open position.

FIGS. 4-7 illustrate the relative positions of the closure flap 12 in the assembled container 6. During use, the closure flap 12 is pivotally movable between a normal closed, unlocked position (not shown), and a fully opened position as shown in FIG. 7. As shown in FIG. 4, the closure flap 12 may be permanently closed and locked for transport and disposal. In the normal closed position, the upper portion 62 of the closure flap does not touch the upper wall 16 of the lid 10; the container is never fully closed and locked until the hooks 36 are inserted into through slots 34 at which point the container 6 is locked for transport and disposal. When in the locked position, the upper portion 62 of the closure flap 12 rests against the front portion 16a of the upper wall 16 of the lid 10 and the closure flap detent 72 rests against the interior downward projection 30.

The closure flap 12 includes a lower portion 60, an upper portion 62, and side portions/walls 64 as well as interior 66 and exterior 68 surfaces. The upper portion 62 of the closure flap 12 includes a central tab 70, which is operable by a user to displace the closure flap 12 between normal closed and open positions. When the tab 70 is pivotally directed downward toward the front shelf 22, the closure flap 12 opens. When released, the closure flap 12 returns to its normal closed position. A detent 72 is provided is provided adjacent to the upper flap portion 62, which when the closure flap 12 is in a permanently locked position rests against the downward projection 30 of an interior upper wall 16 of the lid 10. With respect to the interior surface 66 of the closure flap, the detent 72 provides an inclined surface 74 which works with gravity to direct sharps into the container 6 when the closure flap 12 is moved from an open position to a normal closed position.

The pivotal operation of the closure flap 12 is provided by a plurality of annular axial hubs 42 located at the side edges 64 of the flap in spaced relation with the upper portion 62 of the closure flap 12 such that the mass of lower portion 60 of the closure flap 12 exceeds the mass of the upper portion 62 with the result that the closure flap 12 is gravitationally biased to its normal closed position when released.

Figure 13:
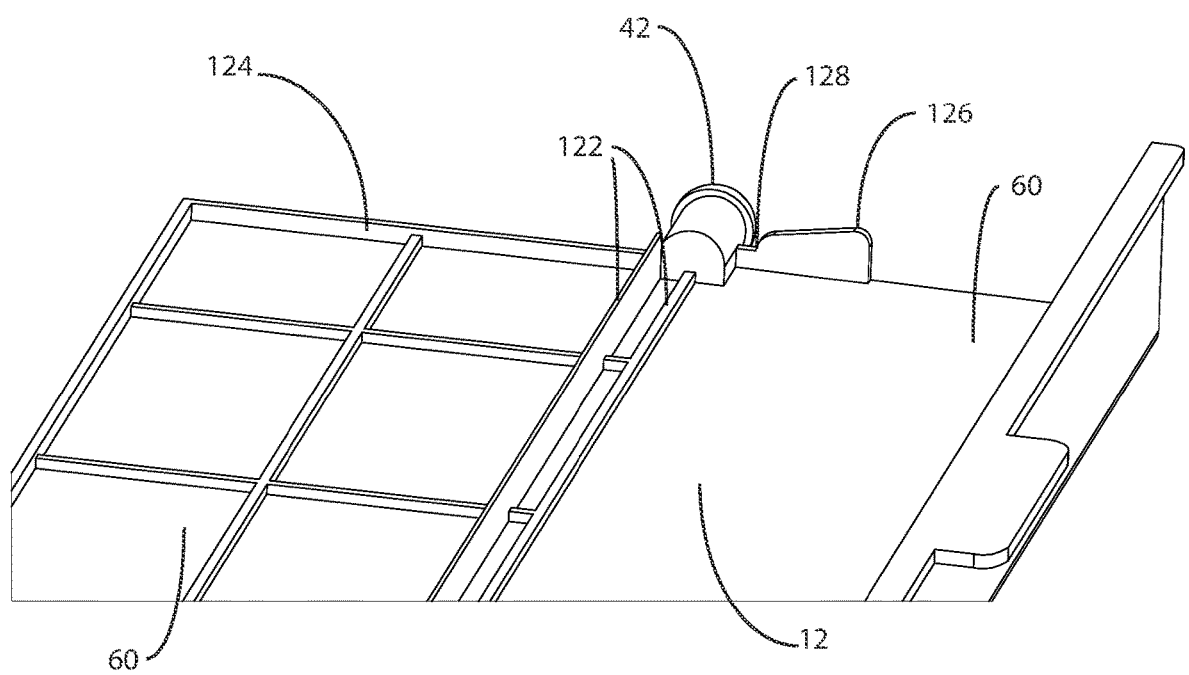
FIG. 13 is partial perspective view of an underside of a closure flap of the container.

As shown in FIG. 13, the closure flap 12 may include various ribs that provide structural rigidity to the closure flap. For example, the flap may include one or more ribs 122 extending across the flap 12 between hubs 42. The flap may also include additional ribs arranged in various appropriate patterns on other portions of the flap. FIG. 13 illustrates, for example, ribs 124 arranged in a generally rectangular pattern across an underside of the lower portion 60 of the flap. In addition, the flap 12 may include a rib 126 that extends from the hub 42 along an edge of the upper portion 62. This rib 126 may include a notch 128 that aids in the installation of the flap 12 into the lid.

Figure 10:
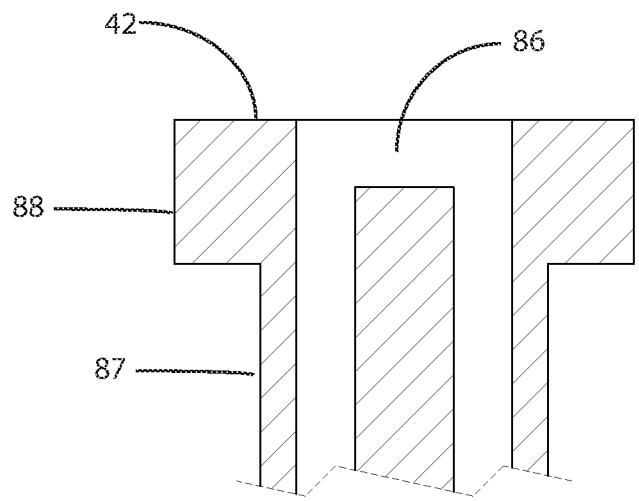
FIG. 10 is a cross-sectional view of the axial hub of the closure flap.

As illustrated in FIGS. 8-10, axial hubs 42 are inserted through openings 38 in the lid 10. The axial hubs 42 include a bearing surface 87 and a flange 88. The flange has a larger diameter than the bearing surface 87. The openings 38 include a circular portion 39 at an upper end of the opening and a generally rectangular lower portion 41. The lower opening portion 41 may extend through the side wall 18 as well as the skirt 26 adjacent the side wall. In this manner, the hub 42 can be inserted through the lower opening 41 and slid upward such that the hub bearing surface 87 engages with the circular opening 39. The circular opening 39 has a diameter that is less that the hub flange 88 so that the flange engages an outside surface of wall 18 adjacent to the semicircular opening 39. The semicircular opening 39 may extend over an arc of 90 degrees, an arc of 180 degrees or an arc of greater than 180 degrees so as to have a snap fit the hub bearing surface 87.

Snap fit covers 14 are provided to maintain the axial hubs 42 in position once inserted through the through openings 38 of the lid 10. The covers 14 include an exterior wall 76, an interior wall 78, side walls 80 and lower wall 82. Locking tabs 44 extending from the side walls 78 in spaced relation with the lower wall 82 and an annular bushing 84 extends from the interior wall 78. After the axial hubs 42 of the closure flap 12 are inserted into the through openings 38 from the interior of the lid 10, the annular bushings 84 of the covers 14 are aligned with the annular opening 86 of the axial hubs 42 and the locking tabs 44 are aligned with the through openings 40 of the lid 10. The diameter of the annular bushing 84 is sized for insertion into the annular opening 86 of the axial hub 42. Once aligned and snapped in place, the cover 14 provides the structural support for the pivotal rotation of the closure flap 12.

What is claimed is:

1. A container for disposal of medical waste comprising:
a cabinet comprising a first wall; and
a disposable container positioned within the cabinet, the disposable container comprising:
   a receptacle having an open top, a bottom wall and a side wall;
   a lid attached to the receptacle, the lid comprising an opening sized to permit the introduction of medical waste into the receptacle and a side wall; and
   a closure flap movable between an open position and a closed position, the closure flap comprising an axial hub extending from the closure flap through an opening in the lid side wall;
wherein the cabinet first wall covers the closure flap axial hub; and
wherein the cabinet first wall comprises a side wall and the container lid comprises a top wall, and wherein an upper edge of the cabinet side wall is coplanar with the disposable container lid top wall.

2. The container of claim 1 wherein the cabinet further comprises a front wall, the front wall comprising a sloped portion angled such that a top end of the sloped portion aligns with an upper portion of the disposable container lid closure flap when the closure flap is in a closed and locked position.

3. The container of claim 2 wherein a bottom end of the sloped portion aligns below the upper portion of the closure flap when the closure flap is in an open position.

4. The container of claim 2 wherein a front portion of the lid side wall comprises a sloped portion that extends parallel to the cabinet front wall sloped portion.

5. The container of claim 1 wherein the disposable container lid comprises a shelf that is positioned below the closure flap axial hub.

6. The container of claim 5 wherein the shelf provides a deck upon which the closure flap rests when in the closure flap is in the open position.

7. The container of claim 1 wherein the disposable container lid top wall is planar.

8. The container of claim 1 wherein the disposable container lid top wall comprises an exterior rib.

9. The container of claim 8 wherein the exterior rib increases the structural rigidity of the lid top wall.

10. The container of claim 8 wherein the rib forms a circular pattern.

11. The container of claim 1 wherein the disposable container lid top wall comprises a plurality of ribs.

12. The container of claim 11 wherein the plurality of ribs form a cross-hatch pattern.

13. The container of claim 1 wherein the disposable container lid comprises a skirt extending from a base of the disposable container lid side wall.

14. The container of claim 13 wherein the disposable container lid comprises a side wall rib extending from the disposable container lid side wall.

15. The container of claim 14 wherein the side wall rib bridges a gap between the lid side wall and the lid skirt.

16. The container of claim 15 wherein the side wall rib provides additional structural integrity to the lid.

17. The container of claim 1 wherein the disposable container lid top wall comprises an interior downward projection.

18. The container of claim 17 wherein a portion of the disposable container closure flap rests against the interior downward projection when the closure flap is in a locked position.

* * * * *